(12) United States Patent
Stad et al.

(10) Patent No.: US 8,377,072 B2
(45) Date of Patent: Feb. 19, 2013

(54) MEDICAL DEVICE INSTALLATION TOOL

(75) Inventors: Shawn Stad, Fall River, MA (US);
Thomas Martin, Riverside, RI (US);
Shinikequa White, Dorchester, MA (US); Thomas Gamache, Fall River, MA (US)

(73) Assignee: DePuy Spine, Inc., Raynham, MA (US)

( * ) Notice: Subject to any disclaimer, the term of this patent is extended or adjusted under 35 U.S.C. 154(b) by 1047 days.

(21) Appl. No.: 11/347,991

(22) Filed: Feb. 6, 2006

(65) Prior Publication Data
US 2007/0185375 A1 Aug. 9, 2007

(51) Int. Cl.
*A61B 17/56* (2006.01)
(52) U.S. Cl. ............................... 606/99; 606/90
(58) Field of Classification Search ............... 606/86 A, 606/99, 90
See application file for complete search history.

(56) References Cited

U.S. PATENT DOCUMENTS

| | | | |
|---|---|---|---|
| 1,934,818 A * | 11/1933 | Richter | 606/113 |
| 2,102,602 A * | 12/1937 | Nash | 269/181 |
| 3,486,505 A * | 12/1969 | Morrison | 606/90 |
| 4,034,746 A | 7/1977 | Williams | |
| 4,337,576 A | 7/1982 | Drost et al. | |
| 4,369,788 A | 1/1983 | Goald | |
| 4,444,184 A | 4/1984 | Oretorp | |
| 4,545,374 A | 10/1985 | Jacobson | |
| 4,660,287 A | 4/1987 | Decker | |
| 4,730,613 A | 3/1988 | Gordy | |
| 4,735,202 A | 4/1988 | Williams | |
| 4,772,287 A | 9/1988 | Ray et al. | |
| 4,877,020 A | 10/1989 | Vich | |
| 4,898,161 A | 2/1990 | Grundei | |
| 4,997,432 A | 3/1991 | Keller | |
| 5,015,247 A | 5/1991 | Michaelson | |
| 5,019,081 A | 5/1991 | Watanabe | |
| 5,020,519 A | 6/1991 | Hayes et al. | |
| 5,052,373 A | 10/1991 | Michelson | |
| 5,055,104 A | 10/1991 | Ray | |
| 5,059,194 A | 10/1991 | Michelson | |

(Continued)

FOREIGN PATENT DOCUMENTS

| | | |
|---|---|---|
| DE | 29901611 | 4/1999 |
| DE | 29916078 | 11/1999 |

(Continued)

OTHER PUBLICATIONS

Depuy Motech., "Keystone Graft Instruments Anterior Cervical Techniques," Technical Manual.

(Continued)

*Primary Examiner* — Ellen C Hammond
(74) *Attorney, Agent, or Firm* — Nutter McClennen & Fish LLP

(57) ABSTRACT

Devices for implanting a prosthetic device, such as an artificial spinal implant, are provided. The installation tool can include a body, a pair of opposed levers, an optional implant holder disposed between the levers, a drive rod at least partially disposed within the body and able to be coupled to the implant holder and/or implant, and a female threaded member associated with the body and selectively engageable with the drive rod. As the drive rod translates along a longitudinal axis of the installation tool, the implant holder and/or implant separates the levers and distracts adjacent vertebral bodies to position a prosthetic device therebetween. The implant holder and/or implant can be longitudinally advanced in rotation and/or translation modes.

23 Claims, 12 Drawing Sheets

U.S. PATENT DOCUMENTS

| | | |
|---|---|---|
| 5,122,130 A | 6/1992 | Keller |
| 5,139,507 A | 8/1992 | Dolgin et al. |
| 5,213,112 A | 5/1993 | Niwa et al. |
| 5,254,128 A * | 10/1993 | Mesa ............................ 606/167 |
| 5,292,329 A | 3/1994 | Werner |
| 5,304,119 A | 4/1994 | Balaban et al. |
| 5,306,248 A * | 4/1994 | Barrington ................. 604/97.02 |
| 5,306,309 A | 4/1994 | Wagner et al. |
| 5,314,477 A | 5/1994 | Marnay |
| 5,403,337 A | 4/1995 | Platts |
| 5,423,843 A | 6/1995 | Werner |
| 5,431,658 A * | 7/1995 | Moskovich ...................... 606/99 |
| 5,431,672 A | 7/1995 | Cote et al. |
| 5,443,514 A | 8/1995 | Steffee |
| 5,481,804 A | 1/1996 | Platts |
| 5,484,437 A | 1/1996 | Michelson |
| 5,496,340 A | 3/1996 | Abidin et al. |
| 5,505,732 A | 4/1996 | Michelson |
| 5,531,754 A | 7/1996 | Shackelford, Sr. et al. |
| 5,562,736 A | 10/1996 | Ray et al. |
| 5,569,281 A | 10/1996 | Abidin et al. |
| 5,569,282 A | 10/1996 | Werner |
| 5,571,109 A | 11/1996 | Bertagnoli |
| 5,599,351 A | 2/1997 | Haber et al. |
| 5,620,454 A | 4/1997 | Pierce et al. |
| 5,645,597 A | 7/1997 | Krapiva |
| 5,665,099 A | 9/1997 | Pilo et al. |
| 5,683,407 A | 11/1997 | Jolly et al. |
| 5,683,464 A | 11/1997 | Wagner et al. |
| 5,720,751 A * | 2/1998 | Jackson ....................... 606/86 R |
| 5,722,977 A | 3/1998 | Wilhelmy |
| 5,730,751 A | 3/1998 | Dillon et al. |
| 5,741,253 A | 4/1998 | Michaelson |
| 5,752,968 A | 5/1998 | Jolly et al. |
| 5,766,252 A | 6/1998 | Henry et al. |
| 5,779,724 A | 7/1998 | Werner |
| 5,782,830 A | 7/1998 | Farris |
| 5,792,162 A | 8/1998 | Jolly et al. |
| 5,797,909 A | 8/1998 | Michelson |
| 5,800,438 A | 9/1998 | Tuke et al. |
| 5,827,309 A | 10/1998 | Jolly et al. |
| 5,868,771 A | 2/1999 | Herbert et al. |
| 5,885,299 A | 3/1999 | Winslow et al. |
| 5,885,300 A | 3/1999 | Tokuhashi |
| 5,888,224 A | 3/1999 | Beckers et al. |
| 5,899,901 A | 5/1999 | Middleton |
| 5,908,432 A | 6/1999 | Pan |
| 5,935,151 A | 8/1999 | Broughton et al. |
| 5,944,658 A | 8/1999 | Koros |
| 5,951,564 A | 9/1999 | Schroder et al. |
| 5,957,927 A | 9/1999 | Magee et al. |
| 6,004,326 A | 12/1999 | Castro et al. |
| 6,015,419 A | 1/2000 | Strome et al. |
| 6,022,364 A | 2/2000 | Flumene et al. |
| 6,042,582 A | 3/2000 | Ray |
| 6,063,088 A | 5/2000 | Winslow |
| 6,066,174 A | 5/2000 | Farris |
| 6,080,155 A | 6/2000 | Michelson |
| 6,083,225 A | 7/2000 | Winslow |
| 6,083,228 A | 7/2000 | Michelson |
| 6,096,038 A | 8/2000 | Michelson |
| 6,113,602 A | 9/2000 | Sand |
| 6,117,174 A | 9/2000 | Nolan |
| 6,133,602 A | 10/2000 | Shrivastava et al. |
| RE37,005 E | 12/2000 | Michelson et al. |
| 6,156,040 A | 12/2000 | Yonemura et al. |
| 6,159,212 A | 12/2000 | Schoedinger, III et al. |
| 6,159,215 A | 12/2000 | Urbahns et al. |
| 6,159,244 A | 12/2000 | Suddaby |
| 6,168,601 B1 | 1/2001 | Martini |
| 6,197,033 B1 | 3/2001 | Haid, Jr. et al. |
| 6,200,322 B1 | 3/2001 | Branch et al. |
| 6,220,124 B1 * | 4/2001 | Perkins ............................ 81/174 |
| 6,261,296 B1 | 7/2001 | Aebi |
| 6,267,763 B1 | 7/2001 | Castro |
| 6,277,122 B1 | 8/2001 | McGahan |
| 6,319,257 B1 | 11/2001 | Carignan et al. |
| 6,436,119 B1 | 8/2002 | Erb et al. |
| 6,440,142 B1 | 8/2002 | Ralph et al. |
| 6,478,800 B1 * | 11/2002 | Fraser et al. ..................... 606/99 |
| 6,520,967 B1 | 2/2003 | Cauthen |
| 6,551,316 B1 | 4/2003 | Rinner |
| 6,575,981 B1 | 6/2003 | Boyd et al. |
| 6,582,437 B2 | 6/2003 | Dorchak et al. |
| 6,585,740 B2 | 7/2003 | Schlapfer et al. |
| 6,589,247 B2 | 7/2003 | McGahan et al. |
| 6,599,291 B1 | 7/2003 | Foley et al. |
| 6,648,888 B1 | 11/2003 | Shluzas |
| 6,648,895 B2 | 11/2003 | Burkus et al. |
| 6,652,533 B2 * | 11/2003 | O'Neil .......................... 606/100 |
| 6,663,638 B2 | 12/2003 | Ralph |
| 6,712,825 B2 | 3/2004 | Aebi |
| 6,719,760 B2 | 4/2004 | Dorchak et al. |
| 6,743,234 B2 | 6/2004 | Burkus et al. |
| 6,755,841 B2 * | 6/2004 | Fraser et al. ..................... 606/99 |
| 6,814,737 B2 | 11/2004 | Cauthen |
| 6,902,566 B2 * | 6/2005 | Zucherman et al. ........ 606/86 A |
| 6,923,814 B1 | 8/2005 | Hildebrand et al. |
| 7,081,118 B2 | 7/2006 | Weber et al. |
| 7,118,580 B1 | 10/2006 | Beyersdorff et al. |
| 7,320,689 B2 * | 1/2008 | Keller ............................ 606/99 |
| 2001/0029377 A1 | 10/2001 | Aebi |
| 2001/0031968 A1 | 10/2001 | Dorchak et al. |
| 2001/0031969 A1 | 10/2001 | Aebi et al. |
| 2002/0072752 A1 | 6/2002 | Zucherman et al. |
| 2002/0123754 A1 | 9/2002 | Holmes et al. |
| 2002/0143343 A1 | 10/2002 | Castro |
| 2002/0198532 A1 | 12/2002 | Michelson |
| 2003/0069586 A1 | 4/2003 | Errico et al. |
| 2003/0078590 A1 | 4/2003 | Errico et al. |
| 2003/0130667 A1 | 7/2003 | Lin |
| 2003/0149438 A1 | 8/2003 | Nichols et al. |
| 2003/0212404 A1 | 11/2003 | Dorchak et al. |
| 2003/0225416 A1 | 12/2003 | Bonvallet et al. |
| 2004/0039397 A1 | 2/2004 | Weber et al. |
| 2004/0078079 A1 | 4/2004 | Foley |
| 2004/0102790 A1 | 5/2004 | Ralph et al. |
| 2004/0106927 A1 | 6/2004 | Ruffner et al. |
| 2004/0117019 A1 | 6/2004 | Trieu et al. |
| 2004/0167535 A1 | 8/2004 | Errico et al. |
| 2004/0167536 A1 | 8/2004 | Errico et al. |
| 2004/0172037 A1 | 9/2004 | Dorchak et al. |
| 2004/0176773 A1 | 9/2004 | Zubok et al. |
| 2004/0215198 A1 | 10/2004 | Marnay et al. |
| 2004/0225295 A1 * | 11/2004 | Zubok et al. ..................... 606/90 |
| 2005/0010213 A1 | 1/2005 | Stad et al. |
| 2005/0027300 A1 | 2/2005 | Hawkins et al. |
| 2005/0043741 A1 | 2/2005 | Michelson |
| 2005/0075644 A1 | 4/2005 | DiPoto et al. |
| 2005/0113842 A1 | 5/2005 | Bertagnoli et al. |
| 2005/0119665 A1 | 6/2005 | Keller |
| 2005/0143747 A1 | 6/2005 | Zubok et al. |
| 2005/0149036 A1 | 7/2005 | Varieur et al. |
| 2005/0159756 A1 | 7/2005 | Ray |
| 2005/0165408 A1 * | 7/2005 | Puno et al. ..................... 606/99 |
| 2006/0025777 A1 | 2/2006 | Weber |
| 2006/0195097 A1 | 8/2006 | Evans et al. |
| 2006/0293692 A1 * | 12/2006 | Whipple et al. .............. 606/104 |
| 2007/0016221 A1 | 1/2007 | Beyersdorff et al. |
| 2007/0123907 A1 | 5/2007 | Weber |
| 2007/0208345 A1 | 9/2007 | Marnay et al. |
| 2007/0208346 A1 | 9/2007 | Marnay et al. |
| 2008/0243190 A1 * | 10/2008 | Dziedzic et al. .............. 606/278 |
| 2008/0262504 A1 | 10/2008 | Ralph et al. |
| 2009/0138091 A1 | 5/2009 | Ray |
| 2009/0209967 A1 | 8/2009 | Evans et al. |
| 2009/0312765 A1 | 12/2009 | Zubok et al. |
| 2010/0069914 A1 | 3/2010 | Puno et al. |
| 2010/0249792 A1 | 9/2010 | Bonvallet et al. |

FOREIGN PATENT DOCUMENTS

| | | |
|---|---|---|
| DE | 20012549 | 10/2000 |
| EP | 0880938 | 12/1998 |

OTHER PUBLICATIONS

Rutsky, V.V. and Valkav, A.N., "Designing a dynamic spinal distractor," Med Tekh. 4:29-32 (1995).

SynMesh System, Original Instruments and Implants of the Associate for the Study of Internal Fixation.

Demetropoulas, C.K., Truumees, E., Herkowitz, H.N. and Yang, K.H., "Development and calivration of a load sensing cervical distractor capable of withstanding autoclave sterilization," Med Eng Phys. 27(4):343-6 (2005).

Spinal Correction FRA Spacer Instruments, pp. 2-10.

Metronic, "Parallel Tissue Offerings," (2004).

Metronic Sofamor Danek, "Catalyst Anterior Instrument Set," pp. 1-10 (2004).

Capasso, G. Velotti A. and Auzino, G., "Mechanical Behavior of Two Types of Vertebral Distractors Submitted to Compression-Flexion Tests," Ital J. Orthop Traumatol. 13(1):121-6 (1987).

* cited by examiner

MEDICAL DEVICE INSTALLATION TOOL

FIELD OF THE INVENTION

The invention relates broadly to a tool for inserting a prosthesis within a body, and more particularly to a tool for inserting prostheses, such as artificial discs or other implants within an intervertebral space.

BACKGROUND OF THE INVENTION

Spinal surgery involves many challenges as the long-term health and mobility of the patient often depends on the surgeon's technique and precision. One type of spinal surgery involves the removal of the natural disc tissue that is located between adjacent vertebral bodies. Procedures are known in which the natural, damaged disc tissue is replaced with an interbody cage or fusion device, or with a disc prosthesis.

The insertion of an article, such as an artificial disc prosthesis, presents the surgeon with several challenges. The adjacent vertebral bodies collapse upon each other once the natural disc tissue is removed. These bodies must be separated to an extent sufficient to enable the placement of the prosthesis. However, if the vertebral bodies are separated, or distracted, to beyond a certain degree, further injury can occur. The disc prosthesis must also be properly positioned between the adjacent vertebral bodies. Over-insertion or under-insertion of the prosthesis can lead to pain, postural problems and/or limited mobility or freedom of movement.

Specialized tools have been developed to facilitate the placement of devices, such as disc prostheses, between adjacent vertebral bodies of a patient's spine. Among the known tools for performing such procedures are separate spinal distractors and insertion devices. The use of separate tools to distract the vertebral bodies and insert a disc prosthesis or graft can prove cumbersome. Further, the use of some distractors can cause over-distraction of the vertebral bodies.

Despite existing tools and technologies, there remains a need to provide a device to facilitate the proper and convenient insertion of an object, such as a disc prosthesis, between adjacent vertebral bodies while minimizing the risk of further injury to the patient.

SUMMARY OF THE INVENTION

The present invention generally provides devices for facilitating the proper and convenient insertion of an object, such as a disc prosthesis, between adjacent vertebral bodies. In one embodiment, a medical device installation tool can include a body, a drive rod, a pair of opposed levers, and a female threaded member associated with the body. The drive rod can be adapted to extend through a bore in the body and can further include threads formed on at least a portion thereof. The opposed levers can each have a proximal and distal end, the proximal end of each lever being pivotally coupled to a portion of the body. The female threaded member can be selectively engageable in a drive rod rotation configuration in which the female threaded member is engaged with the threads on the drive rod to permit longitudinal translation of the rod upon rotation of the rod and a translation configuration in which the female threaded member is disengaged from the threads on the drive rod to permit longitudinal translation of the rod without rotation of the rod. Optionally, the levers can be removably and replaceably coupled to the body.

In another embodiment, a medical device installation tool can be adapted to engage an implant or implant holder disposed at the distal end of the drive rod. The implant holder can optionally include a selectively adjustable height.

In yet another embodiment, a handle component can be disposed at either the proximal or distal end of the body. Where the handle is disposed at the distal end of the body, opposed sides of the handle can have a groove formed thereon with a coupling flange disposed at a proximal portion of each groove and a stabilizing flange disposed at a distal portion of each groove. In this embodiment, each lever can have a slot formed in at least a portion of an inwardly facing side thereof that is adapted to seat the stabilizing flange.

In one embodiment, the female threaded member can be a split nut having two separate sections with each section including a substantially hemispherical groove extending axially therethrough. Each hemispherical groove can have threads formed on at least a portion thereof. The separate sections can be biased to a joined position such that the hemispherical grooves are aligned to form a substantially cylindrical bore and the threads in the grooves are adapted to mate with the threads on the drive rod. The installation tool of this embodiment can also include a release mechanism adapted to separate the separate sections such that the threads in the grooves are unable to mate with the threads on the drive rod. In another embodiment, the separate sections can be biased to a separated position in which the threads in the grooves are unable to mate with the threads on the drive rod, and an engagement mechanism is provided to urge the threads in the grooves into mating contact with the threads on the drive rod.

In yet another embodiment, the female threaded member can be a half nut having a substantially hemispherical groove extending axially therethrough. The hemispherical groove can have threads formed on at least a portion thereof. The installation tool of this embodiment can include an engagement member adapted to maintain the threads of the hemispherical groove in mating contact with the threads of the drive rod. In one embodiment, the engagement member can be biased to a position in which it is effective to urge the threads in the groove into mating contact with the threads of the drive rod. In this embodiment, the installation tool can include a release mechanism adapted to separate the separate sections such that the threads in the groove are unable to mate with the threads on the drive rod. In another embodiment, the engagement member can be biased to a position in which it is effective to separate the separate sections, and the release mechanism is adapted to urge the threads in the groove into mating contact with the threads on the drive rod.

In a further embodiment, the medical device installation tool, comprises a body having a bore extending therethrough; a drive rod adapted to extend through the bore, wherein the drive rod has a proximal end and a distal end with threads formed on at least a portion of a surface thereof. The tool also includes a pair of opposed levers, each having a proximal end and a distal end, the proximal end of each lever being pivotally coupled to a portion of the body. Further, the body has at least a partial female thread formed in at least a portion of the bore, wherein the female thread is selectively engageable in (1) a drive rod rotation configuration in which the female thread is engaged with the threads on the rod to permit longitudinal translation of the rod upon rotation of the rod and (2) a translation configuration in which the female thread is disengaged from the threads on the rod to permit longitudinal translation of the rod upon translation of the rod without rotation of the rod.

A method for implanting a prosthetic device, comprises disposing portions of opposed, pivotable levers of an installation tool between vertebral bodies; advancing the prosthesis toward a distal end of the installation tool by longitudinal movement of the drive rod without rotation of the drive rod; establishing a threaded connection between a portion of the drive rod and a portion of the installation tool to enable longitudinal translation of the prosthesis upon rotation of the drive rod; and rotating the drive rod to longitudinally advance the prosthesis to an implantation site.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
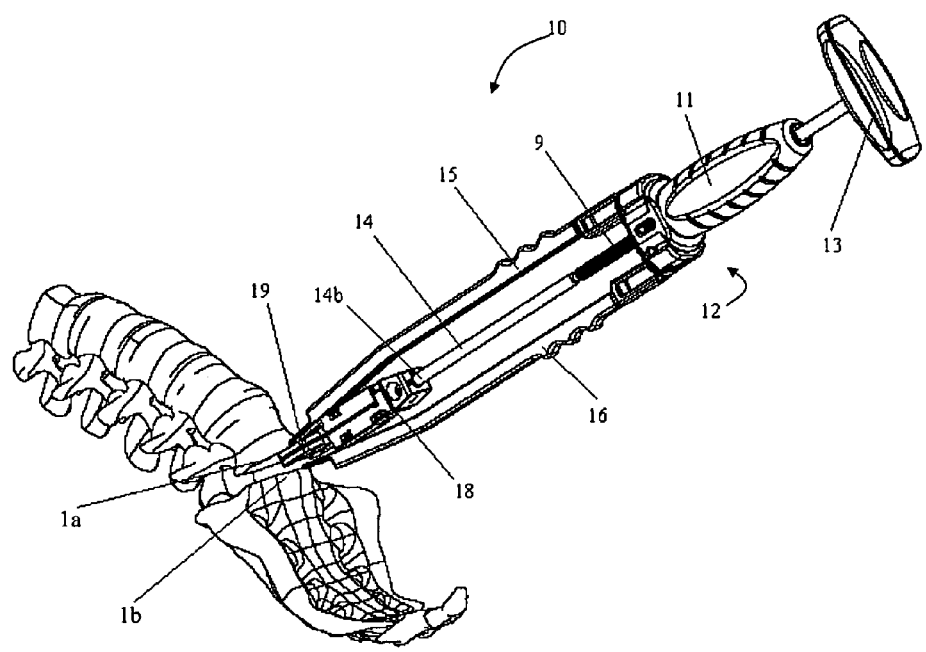
FIG. 1 is a perspective view of one embodiment of an installation tool in use to insert a prosthesis between adjacent vertebrae, distracting adjacent vertebrae.

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention provides a medical device installation tool 10 for implanting a prosthetic device, such as a spinal implant 19, between adjacent vertebral bodies 1a, 1b. In general, and referring to FIG. 1, the installation tool 10 includes a body 12 from which a pair of opposed levers 15, 16 extend distally. The installation tool 10 also includes a drive rod 14 that is at least partially disposed within the body 12 and has threads 9 formed on at least a portion of an external surface thereof. In one aspect, an implant holder 18 can be coupled to a distal end 14b of the drive rod 14 and a handle 13 can be attached to a proximal end 14a of the drive rod. The implant holder 18 is, in turn, adapted to be disposed between the levers 15, 16, and distal movement of the implant holder 18 between the levers 15, 16 causes separation of the levers 15, 16 by the implant holder 18 and/or the implant 19 acting on the levers 15, 16. Alternatively, the distal end 14b of the drive rod 14 can be attached directly to an implant 19, which is adapted to be positioned between the levers 15, 16, and distal movement of the implant 19 between the levers 15, 16 causes separation of the levers 15, 16. The installation tool can be configured such that the implant 19 and/or implant holder 18 can be advanced either by rotating the drive rod 14 or by disengaging the body 12 from the threads 9 on the drive rod 14 to permit longitudinal translation of the rod 14 without rotation.

Figure 10:
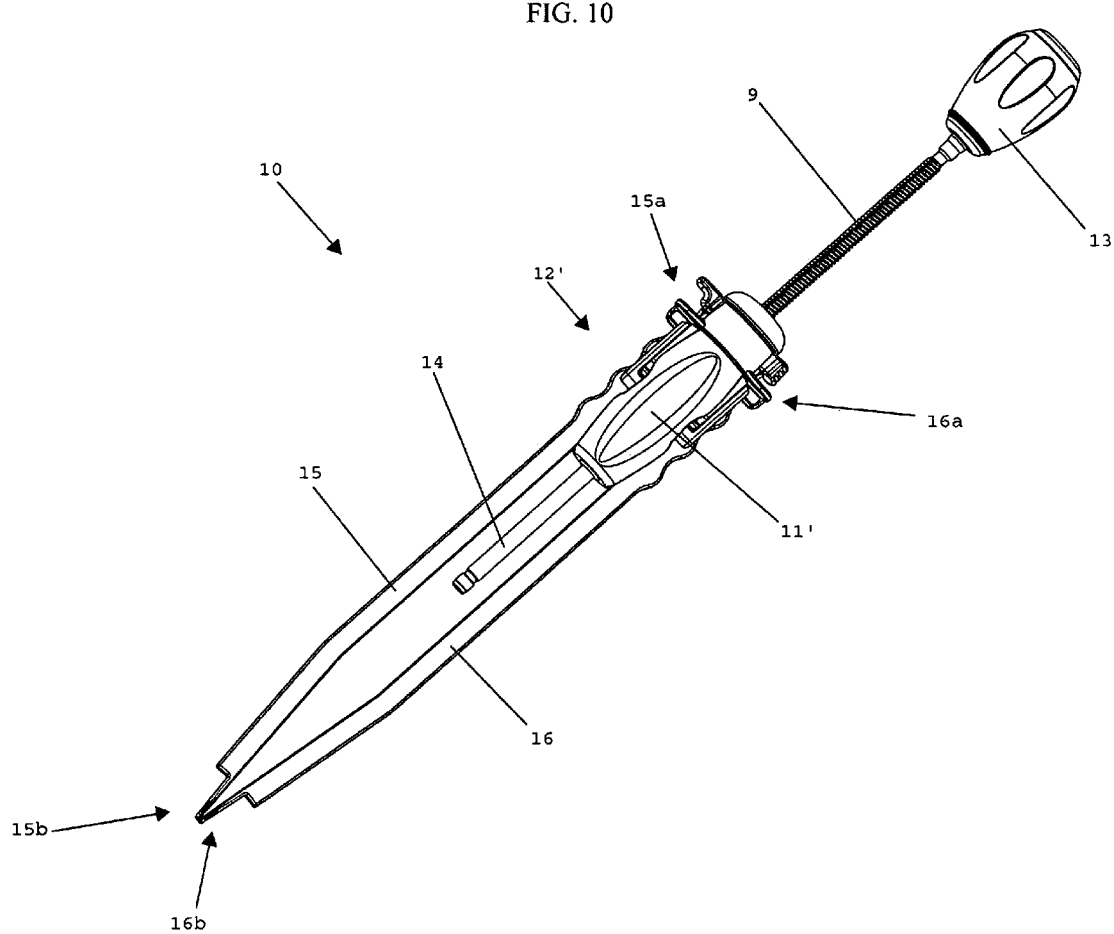
FIG. 10 is a perspective view of another embodiment of an installation tool.
Figure 11:
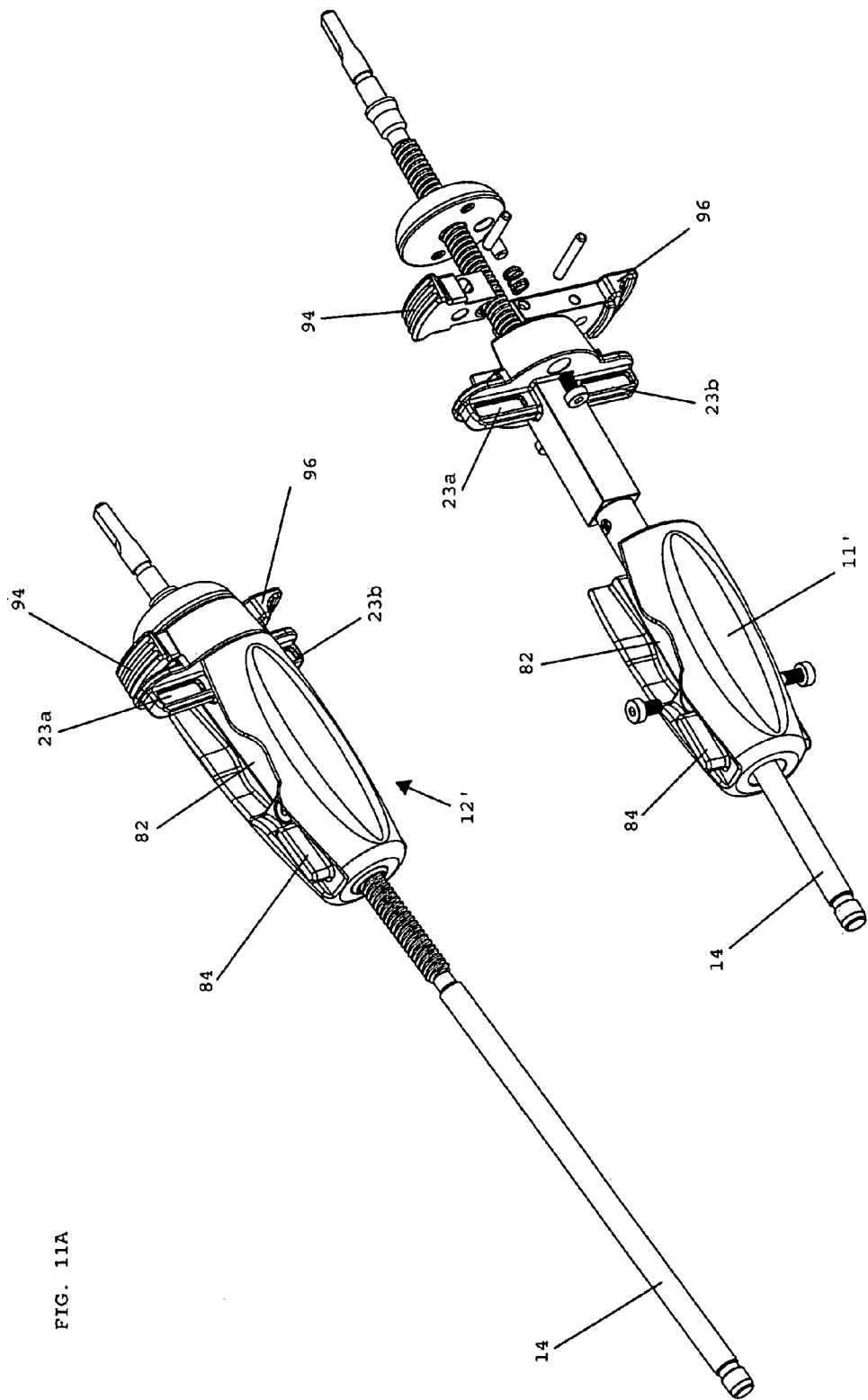
FIG. 11A is a perspective view of selected components of the installation tool of FIG. 10.
FIG. 11B is an assembly view of the portion of the installation tool shown in FIG. 11A.
Figure 12:
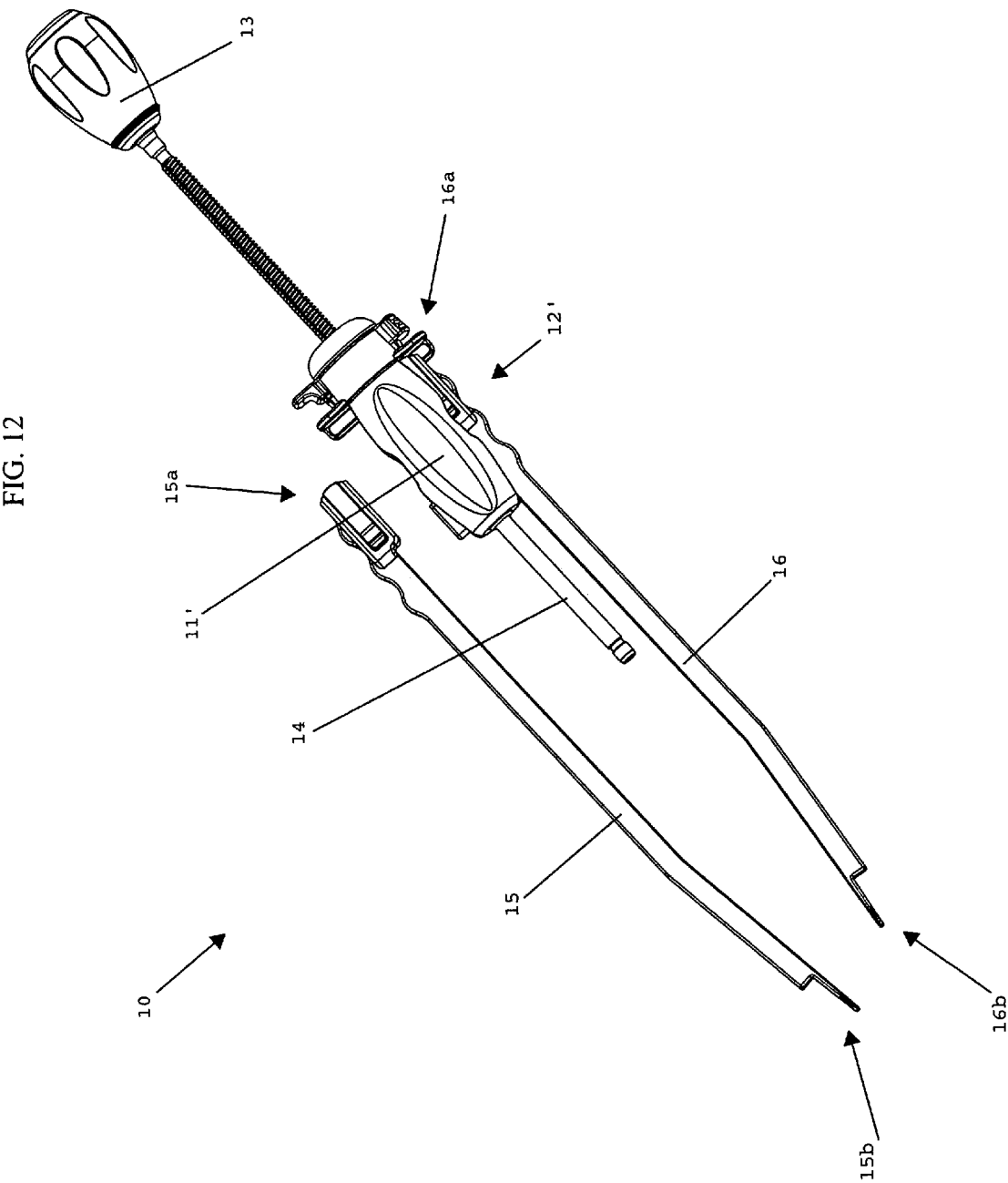
FIG. 12 is a perspective view of a partially assembled installation tool of the type shown in FIG. 10.

In one embodiment, shown in FIGS. 1-8, the body 12 includes a handle component 11 at a proximal end thereof and a housing portion 17, that includes a female threaded member 28, disposed distally of the handle 11. One or more coupling flanges 23a, 23b may be attached to a distal facing surface 25 of the housing portion 17. A pair of levers can be removably attached to the coupling flanges 23a, 23b as will be explained below, or optionally, the levers can be permanently attached. The handle 11 can be coupled to the housing portion 17, or these two components can be separate, but adapted to be positioned adjacent to each other. One skilled in the art will appreciate that the positional relationship of the handle component with respect to the body can be reversed. For example, as illustrated in FIGS. 10-12, described below in more detail, the handle component 11 can be disposed at a distal end of the body 12.

Figure 5:
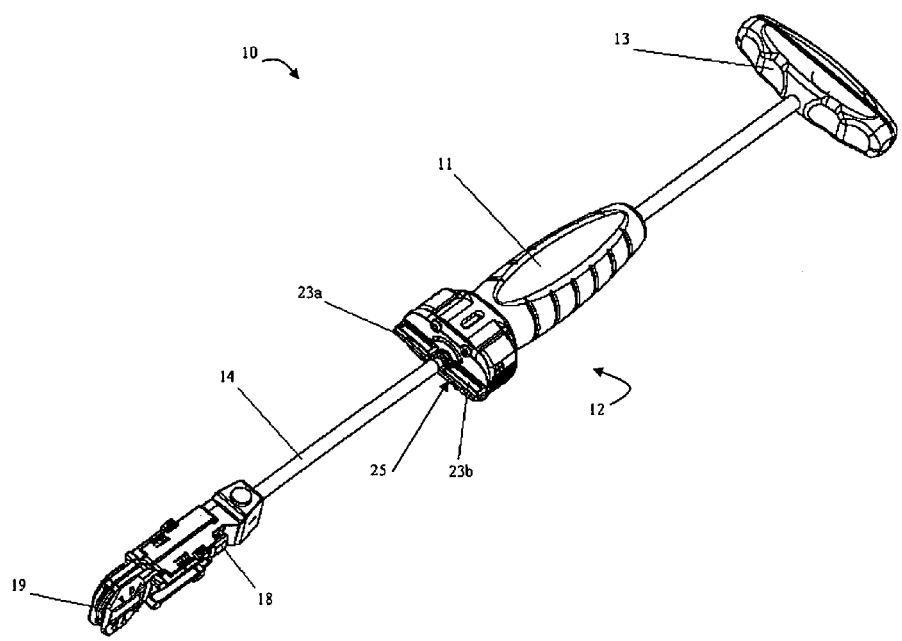
FIG. 5 is a perspective view of a portion of the installation tool shown in FIG. 1 with opposed levers removed.
Figure 7A:
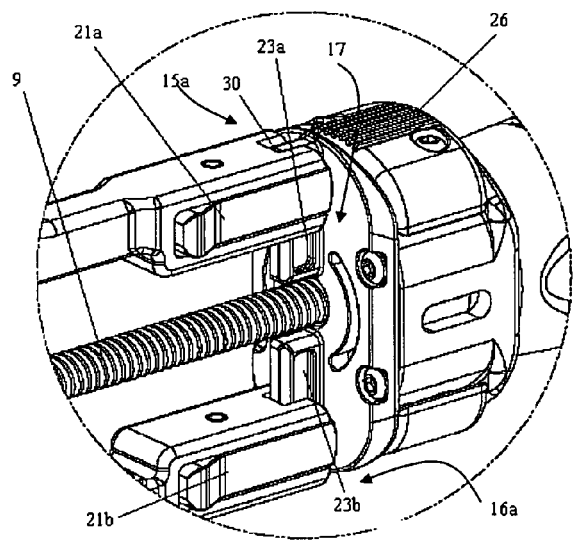
FIG. 7A is a detailed perspective view of a portion of the installation tool shown in FIG. 3.
Figure 8:
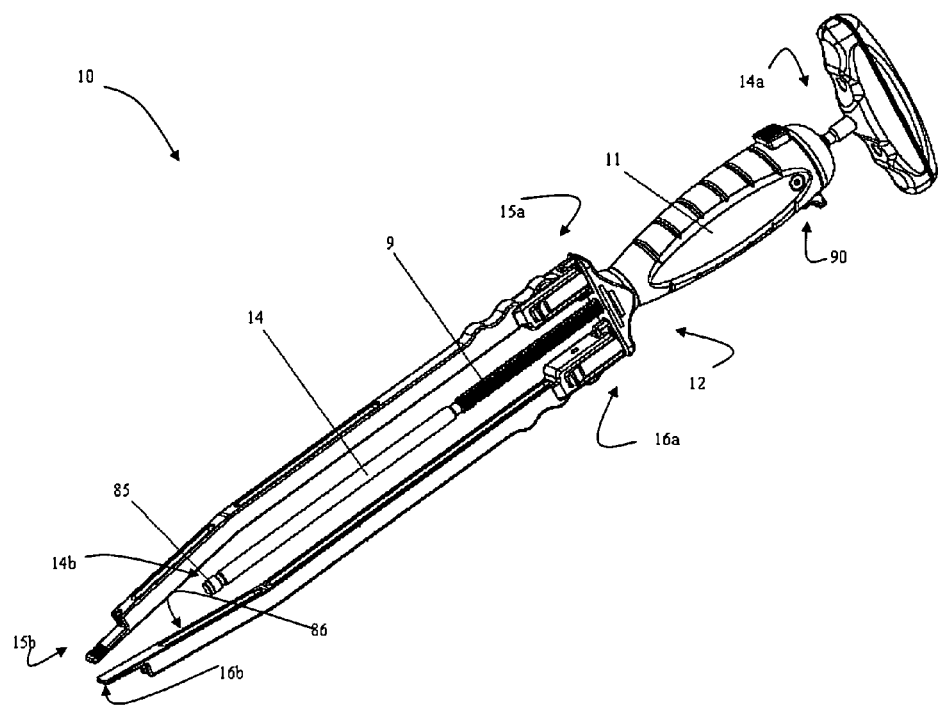
FIG. 8 is a perspective view of another embodiment of an installation tool without an implant holder.

The opposed first and second levers 15, 16 each have a proximal end 15a, 16a and a distal end 15b, 16b, respectively. As shown in FIGS. 7A and 8, the proximal ends 15a, 16a of each lever 15, 16 can include a mating groove 30 within which a coupling flange 23a, 23b can seat. A locking mechanism, such as engagement members 21a, 21b, can secure the coupling flanges 23a, 23b within grooves 30. The engagement member 21a, 21b is configured such that the levers 15, 16 can be removably coupled to the body 12 of the installation tool 10 to allow attachment of various types of levers to the body, such as levers having varying sizes and geometries. This feature also enables the installation tool 10 to be used without the opposed levers 15, 16, for example as shown in FIG. 5, in the event that the levers are not needed to distract the vertebral bodies. The coupling of the levers 15, 16 to body 12 is such that the levers are able to pivot upon the body such that the distal ends 15b, 16b of the levers are able to separate to distract adjacent vertebrae and to allow passage of implant holder 18 and/or implant 19 therebetween. Such pivotal movement can be accommodated, for example, by utilizing levers having slightly rounded proximal ends 15a, 16a. In addition, coupling flanges 23a, 23b can be oriented in a direction transverse to a longitudinal axis (x) of tool 10. One skilled in the art will appreciate that the coupling of the levers 15, 16 to the body 12 can also be done in such a way as to allow some play (e.g., linear movement) to facilitate convenient use and to accommodate anatomical features or irregularities.

Figure 2:
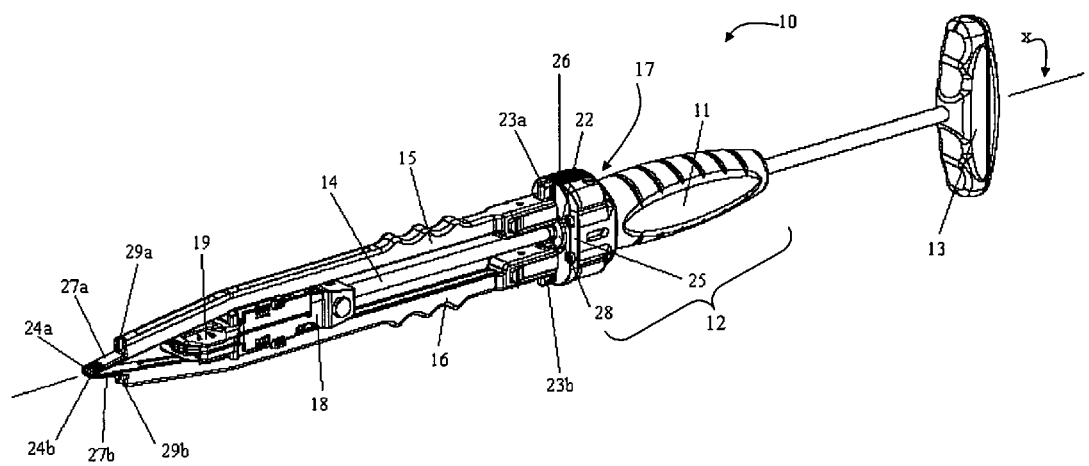
FIG. 2 is a perspective view of the installation tool shown in FIG. 1 with an implant in a retracted position.
Figure 3:
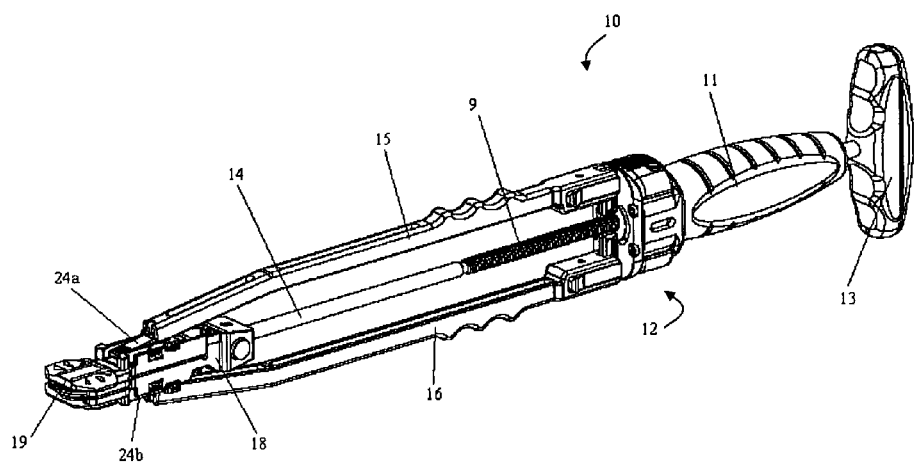
FIG. 3 is a perspective view of the installation tool shown in FIG. 1 with an implant in an advanced position.
Figure 4:
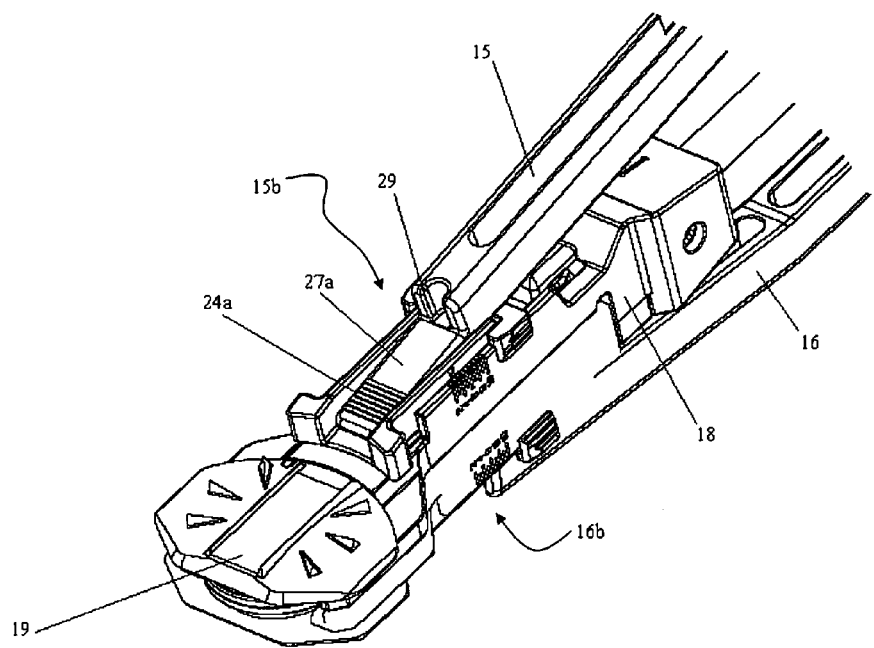
FIG. 4 is a perspective view of the distal end of the installation tool shown in FIG. 3.

Referring to FIGS. 2-4, the distal ends of 15b, 16b of the levers 15, 16 can include blade tips 24a, 24b sized and configured to facilitate their placement between vertebral bodies.

The blade tips 24a, 24b include outwardly facing surfaces 27a, 27b that can be beveled or radiused. In one embodiment, outwardly facing surfaces 27a, 27b can be substantially curved or angled in a superior or inferior direction to facilitate placement of the blade tips 24a, 24b between adjacent vertebrae. Certain surface features may be present on surfaces 27a, 27b to enhance boney purchase. For example, surfaces 27a, 27b may include teeth, serrations, or other roughened features.

As FIG. 4 illustrates, the distal ends 15b, 16b of the levers 15, 16 can include stop surfaces 29 disposed adjacent to the blade tips 24a, 24b. The stop surfaces 29 can be configured to abut a vertebral body during a surgical procedure for installing a prosthesis, such as an artificial disc, between adjacent vertebral bodies. The stop surfaces 29 can have a variety of geometric configurations. However, as illustrated, the stop surfaces 29 can be substantially perpendicular to the blade tips 24a, 24b when viewed in the vertical plane. In another embodiment, the stop surfaces 29 can have a substantially concave profile when viewed in the vertical plane.

The inwardly facing sides of the levers 15, 16 are adapted and configured to allow a prosthetic device to be positioned and guided therebetween. For example, in one embodiment the inwardly facing side of the levers 15, 16 can include substantially planar surfaces that can guide and/or support the implant 19 as it moves distally along the levers 15, 16. In another embodiment, the inwardly facing side of the levers 15, 16 can be configured to support a portion of an implant holder 18 and/or an implant. For example, as shown in FIG. 8, the inwardly facing side of each lever can also include a slot 86 within which a portion of the implant holder 18 or the implant 19 can be slidably seated.

As noted above, the drive rod 14 extends through a bore 22 formed in the components of the body 12. The drive rod can be in the form of an elongate member, a distal portion 14b of which is disposed between the levers 15, 16. The distal end 14b of the drive rod 14 can include a coupling mechanism 85 (FIG. 8), such as a threaded or grooved tip, that can be coupled to an implant holder 18 or implant 19. The coupling mechanism 85 can attach to a corresponding coupling mechanism disposed on the implant holder 18 and/or implant 19. For example, the implant holder 18 or implant 19 can include a threaded or grooved bore matable with the threaded or grooved end of the drive rod 14. With such a coupling, forward and rearward motion of the rod 14 will effect corresponding motion of the distal end 14b of the rod 14 along the longitudinal axis (x) of the tool 10 and any implant holder 18 and/or implant 19 attached thereto.

As noted above, the installation tool 10 is designed such that linear translation of an implant holder 18 and/or implant 19 along the levers 15, 16 in a proximal to distal direction causes the opposed levers 15, 16 to separate. Such separation will enable the levers 15, 16 to distract two adjacent bodies during an installation procedure as discussed below.

In one embodiment, the installation tool 10 can include an implant holder 18 which is coupled to the distal end 14b of the rod 14 and disposed between the levers 15, 16. Linear displacement of the rod 14 can cause the implant holder 18 to move between the levers 15, 16 in a proximal to distal direction. As the implant holder 18 (and any attached implant 19) moves distally, it can come into contact with the inwardly facing sides of the levers 15, 16 causing the distal end 15b, 16b of the levers 15, 16 and the blade tips 24a, 24b to separate from each other. For example, as shown in FIG. 2, in a retracted position, the implant holder 18 (and any attached implant 19) is positioned proximal of distal ends 15b, 16b of the levers 15, 16 such that the inwardly facing surfaces of blade tips 24a, 24b are in contact with each other. As the implant holder 18 moves distally, the levers pivot and separate such that the blade tips 24a, 24b distract and become spaced apart from each other, as shown in FIGS. 3 and 4, by a distance to allow the implant holder 18 and/or implant 19 to pass therebetween.

In one embodiment, the size (e.g., height) of the implant 19 can determine the amount of separation required between the blade tips 24a, 24b, and thus the amount of distraction required of the vertebral bodies to implant a prosthesis. That is, a relatively larger implant 19 can require a greater amount of separation between the blade tips 24a, 24b and a corresponding amount of distraction of the vertebral bodies. As a result, the implant holder 18 and/or implant 19 can be configured to have various heights, depending upon the amount of separation required between the blade tips 24a, 24b. One skilled in the art will appreciate that the adjacent vertebrae should only be distracted by an amount sufficient to insert a prosthesis therebetween. Thus, the implant holder 18 should be selected to cause only the minimum amount of distraction necessary to implant a prosthesis. To this end, the tool 10 can be provided with an implant holder 18 having a selectively adjustable height and/or multiple, interchangeable implant holders 18 having different sizes and shapes.

The implant holder 18 can also be configured to allow connection of the distal end 14b of the drive rod 14 to the implant. In one embodiment, the implant holder 18 can include a bore extending therethrough. The drive rod 14 can extend through the bore such that the rod 14 is coupled to the implant holder 18 and such that at least a portion of the coupling mechanism of the rod 14 extends into the implant holder 18. In this embodiment, the coupling mechanism can mate directly to the implant 19, or it can mate to a connector element which, in turn, can mate to the implant 19.

While the implant holder 18 can be configured to allow connection of the distal end 14b of the drive rod 14 to the prosthetic device, the implant holder 18 can have other configurations as well. In one embodiment, the distal end 14b of the drive rod can attach to the implant holder 18 and the implant holder 18 can include a connection mechanism disposed along the face of the implant holder 18 that enables the implant holder 18 to couple directly to the prosthesis device. By way of non-limiting example, the connection mechanism of the implant holder 18 can include a threaded connection, a dovetail connection, a snap-on connection, or a taper lock connection.

In another embodiment, there is no need for an implant holder 18. Instead, the coupling mechanism 85 disposed at the distal end 14b of the drive rod 14 can couple directly to an implant 19, and the implant 19 causes separation of the levers 15, 16 as it travels distally therebetween.

As noted above, the drive rod 14 is at least partially threaded and is adapted to extend through the bore 22 disposed within the body 12 of the installation tool 10. That is, the bore 22 can extend through the housing 17 and handle component 11. The housing 17 includes a mechanism, such as a female threaded member 28, that enables the threads 9 of the drive rod 14 to be selectively engaged or disengaged. When the threads are engaged, the drive rod can move in the axial direction only as a result of rotation of the drive rod. When the threads are disengaged, forward or rearward movement (i.e., linear translation) of rod 14 can be effected without rotation.

Figure 6:
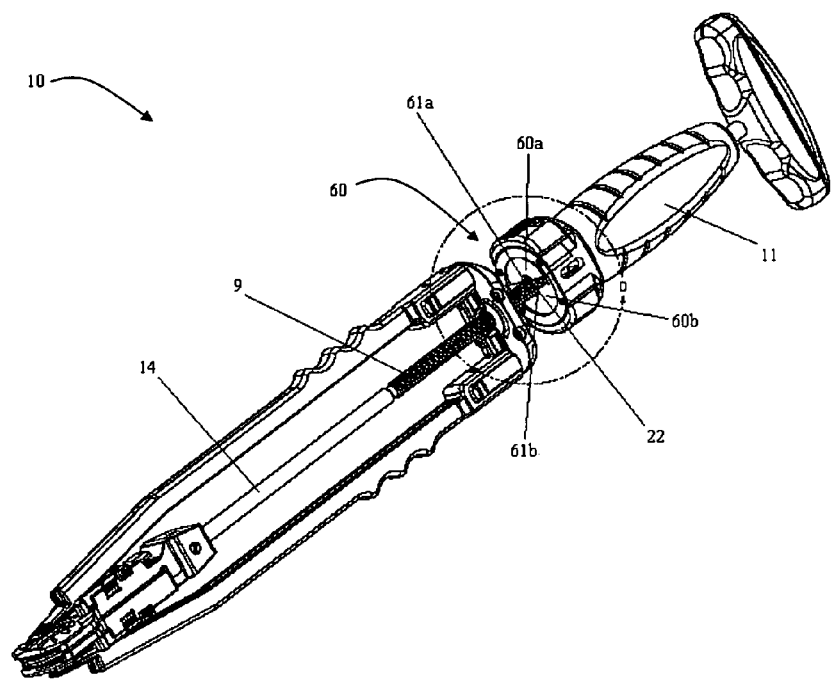
FIG. 6 is a perspective view of one embodiment of a partially assembled installation tool of FIG. 1 having a split nut female threaded member.
Figure 7B:
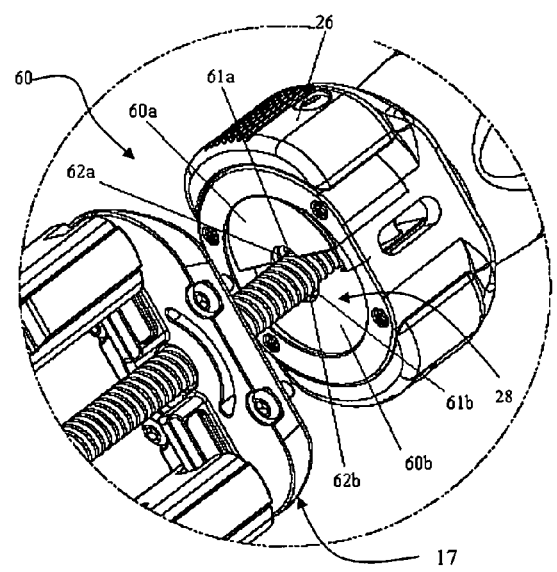
FIG. 7B is a detailed perspective view showing a split nut of the installation tool of FIG. 6.

Referring to FIGS. 6-7B, at least part of bore 22 is defined by female threaded member 28. In the embodiment illustrated in FIGS. 1-7B, best shown in FIGS. 6-7B, the female threaded member 28 is a split nut 60 having two separate sections 60a, 60b. Each section of the split nut 60 includes a substantially hemispherical groove 61a, 61b extending axially therethrough and aligned with the bore 22 in the body 12. The hemispherical groove 61a, 61b has threads 62a, 62b formed on at least a portion thereof. Threads 62a, 62b are complimentary to and are adapted to mate with the threads 9 on the drive rod 14. In one embodiment, the separate sections 60a, 60b can be biased to ajoined position such that the hemispherical grooves 61a, 61b are aligned to form a substantially cylindrical bore and the threads 62a, 62b in the grooves 61a, 61b are in mating contact with the threads 9 on the drive rod 14. This configuration enables longitudinal translation of the rod 14 upon rotation of the rod 14. In this embodiment, the installation tool 10 can include a release mechanism 26 associated with the body 12 and adapted to separate the separate sections 60a, 60b such that the threads 62a, 62b in the grooves 61a, 61b are unable to mate with the threads 9 on the drive rod 14. By disengaging the threads 62a, 62b in the grooves 61a, 61b from the threads 9 on the drive rod 14, longitudinal translation of the drive rod 14 without rotation of the rod 14 is permitted. The release mechanism 26 can be disposed on the body 12 and can include a button, switch or other mechanism to trigger the separation of the threads 62a, 62b on the split nut 60 from the threads 9 on the drive rod 14.

In another embodiment (not shown), the separate sections 60a, 60b can be biased to a separated position in which the threads 62a, 62b in the grooves 61a, 61b are unable to mate with the threads 9 on the drive rod 14 allowing translation of the drive rod 14 without rotation of the rod 14. In this embodiment, an engagement mechanism 26 is adapted to urge the threads 62a, 62b in the grooves 61a, 61b into mating contact with the threads 9 on the drive rod 14 enabling translation of the rod 14 only upon rotation of the rod 14. Similar to the release mechanism, the engagement mechanism can be disposed on the body 12 and can include a button, switch or other mechanism to trigger the engagement of the threads 62a, 62b of the split nut 60 with the threads 9 on the drive rod 14.

Figure 9A:
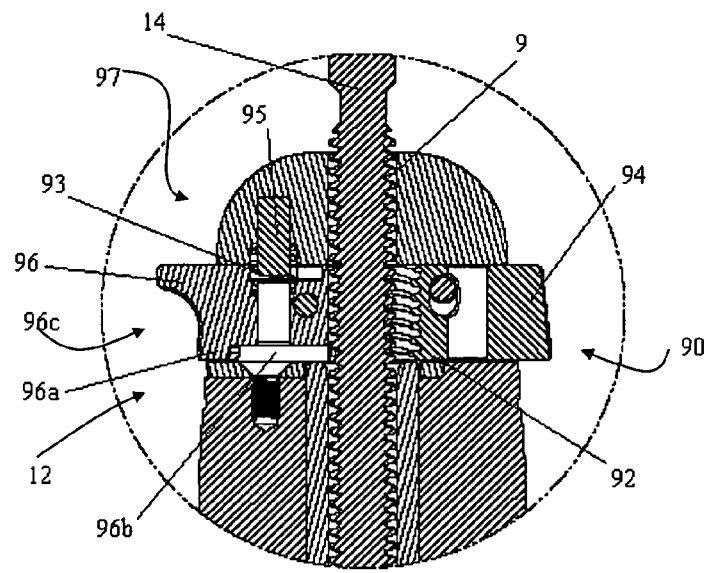
FIG. 9A is a cross-sectional view of a portion of the installation tool of FIG. 8.
Figure 9B:
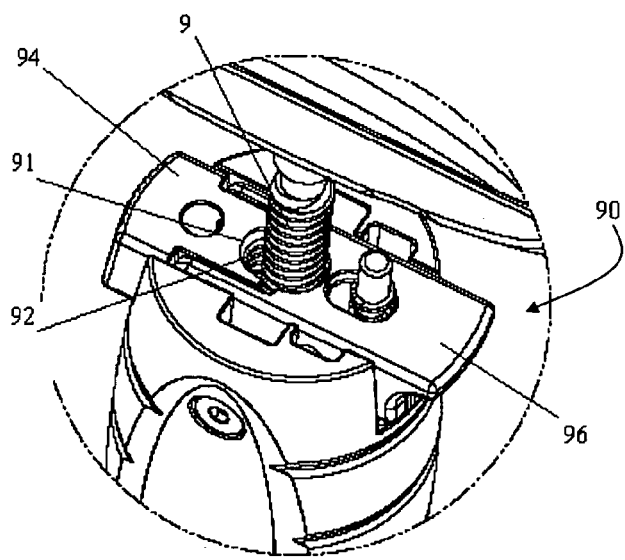
FIG. 9B is a detailed perspective view of a portion of a half nut female threaded member of the installation tool of FIG. 8.

FIGS. 8-12 illustrate another embodiment in which the female threaded member 28 is a half nut 90. With reference to FIGS. 8-9B, half nut 90 has a substantially hemispherical groove 91 extending axially therethrough. As with the split nut embodiment, the hemispherical groove 91 of the half nut is aligned with the bore 22 in the body 12, and at least a portion of the hemispherical groove 91 has threads 92 formed thereon. The half nut embodiment can also include a non-threaded portion of the hemispherical groove 91, which can be opposed to the threaded portion, that can be bored to the major diameter of the threaded portion of the drive rod 14. The half nut embodiment includes an engagement member 94 associated with the body 12 and adapted to maintain the threaded portion 92 of the hemispherical groove 91 in mating contact with the threads 9 on the drive rod 14. In one half nut embodiment, the engagement member 94 is biased to a position in which it is effective to urge the threads 92 of the hemispherical groove 91 into mating contact with the threads 9 on the drive rod 14. As with the split nut embodiment, this configuration enables longitudinal translation of the rod 14 only upon rotation of the rod 14. In this embodiment, the installation tool 10 can include a release mechanism 96 associated with the body 12 and adapted to disengage the threaded portion 92 of the hemispherical groove 91 from the threads 9 on the drive rod 14. When the threads 92 of the hemispherical groove 91 are not in mating contact with the threads 9 on the drive rod 14, as shown in FIG. 9B, longitudinal translation of the drive rod 14 without rotation of the rod 14 is permitted.

One skilled in the art will appreciate that the engagement member 94 can alternatively be biased to a position in which the threaded portion 92 of the hemispherical groove 91 is disengaged from the threads 9 on the drive rod 14. In this embodiment (shown in FIG. 9A), the threads 92 of the hemispherical groove 91 can be urged into mating contact with the threads 9 on the drive rod 14 by applying force to the engagement member 94. Pressing the engagement member 94 inward can cause the release mechanism 96 to move outwardly and lock into an engaged position. For example, in one embodiment, a locking mechanism 97 associated with the half nut 90 can include a spring 93 that is held in position by a stationary pin 95. The spring 93 can be compressed such that it applies a constant downward force on the release mechanism 96. In this embodiment, the release mechanism 96 includes a locking portion 96a and a clearance portion 96b. As force is applied to the engagement member 94, the release mechanism 96 slides outward. Once the locking portion 96a has cleared the sidewall of the installation tool, the release mechanism 96 is forced downward by the spring 93 and locked in place. The locking portion 96a can be adapted to fit against the sidewall of the tool, thereby holding the release mechanism 96 in place and maintaining the thread engagement. To disengage the threads, force can be applied to a scalloped portion 96c of the release mechanism 96 in an upward and inward direction, thereby unlocking the release mechanism 96 and urging the threads 92 of the hemispherical groove 91 away from the threads 9 on the drive rod 14.

It is possible to use various body designs without departing from the scope of invention. FIGS. 1-7B illustrate an embodiment in which the body 12 is relatively small with only minimal surface area contact between body 12 and levers 15, 16. Alternatively, FIGS. 10-12 illustrate an embodiment that affords more surface area contact between the body 12', potentially providing additional stability of the levers. One skilled in the art will appreciate that the half-nut or split nut designs can be used with either body configuration.

With further reference to FIGS. 10-12, the somewhat larger body 12' includes grooves 82 formed on opposed sides of handle component 11', which are adapted to seat the levers 15, 16. The body 12 can also include coupling flanges 23a, 23b disposed thereon at a proximal portion of each groove 82 and a stabilizing flange 84 disposed at a distal portion of each groove 82. As FIG. 12 illustrates, the levers 15, 16 of the stable body embodiment can be removably attached within the grooves 82 such that a portion of each lever seats both the coupling flange 23a, 23b and the stabilizing flange 84.

FIGS. 1-4 illustrate the use of an installation tool 10 for the implantation of a prosthetic device 19, such as an intervertebral implant. As illustrated in FIG. 2, the tool 10 can be assembled in one embodiment with the drive rod 14 coupled to an implant holder 18 and an implant 19 disposed in the holder 18. For example, the tool can be configured in a rotation mode in which rotation of handle 13 will cause the shaft to rotate so that it can be threaded into the implant holder 18. In an initial state, the implant holder 18 can be positioned in proximity to a proximal end 15a, 16a of the levers 15, 16 such that the blade tips 24a, 24b are in a closed or non-distracted state. The blade tips 24a, 24b can then be inserted or wedged between adjacent vertebral bodies 1a, 1b to effect slight separation between the vertebral bodies 1a, 1b. Although not illustrated, one skilled in the art will appreciate that tool 10 can be manipulated such that the blade tips 24a, 24b are fully inserted between the vertebral bodies such that the stop surfaces 29 of the levers 15, 16 can abut a surface of the vertebral bodies. As shown in FIG. 5, the tool 10 can also be used for installation of a prosthetic device without the use of opposed levers 15, 16. In this embodiment, the tool 10 is used only for placement of an implant and not for distraction of the vertebral bodies.

As illustrated in FIG. 3, the drive rod 14 and the implant holder 18 and/or implant 19 can then be advanced distally along the longitudinal axis (x) of the installation tool 10. For example, with the tool 10 in a rotation mode, rotation of the handle 13 disposed at the proximal end of the drive rod 14 will cause the rod 14 to translate along the longitudinal axis and advance the implant holder 18 and/or implant 19 toward the vertebral bodies 1a, 1b. In addition to the rotation mode, the selectively engageable female threaded member 28 allows the surgeon to easily switch from rotation mode to translation mode. Thus, the surgeon can quickly advance the implant 19 to a distal portion of the installation tool 10 in translation mode and switch to rotation mode, once it is necessary to distract blade tips 24a, 24b, for a slower, more precise placement of the implant 19. As a result, the distal movement of the implant holder 18 and/or implant 19 between the levers 15, 16 will cause the blade tips 24a, 24b to distract which, in turn, causes distraction of the vertebral bodies 1a, 1b. Advancement of the implant holder 18 continues until, as shown in FIGS. 3-4, the implant 19 extends beyond the blade tips 24a, 24b and the implant 19 is properly installed between the adjacent vertebral bodies 1a, 1b. When the implant reaches its final position, continued translation of the shaft draws the opposed levers from the disc space leaving only the implant in the disc space. FIGS. 1-3 illustrate that at all times separation of the vertebral bodies is only effected to the extent necessary to insert the prosthetic device. Excessive distraction or separation of the vertebral bodies does not occur because the separation of vertebral bodies is caused by the height of the implant holder 18 and/or implant 19.

If the drive rod 14 is connected directly to an implant 19, continued rotation of the rod 14 after placement of the implant 19 will decouple the rod 14 from the implant 19. Once the drive rod 14 has been disconnected from the implant 19, the insertion tool 10 can be removed from between the adjacent vertebral bodies 1a, 1b. For example, this feature can be useful to install a trial implant without impaction. The drive rod can be coupled directly to the trial. Continued rotation of the rod after placement will withdraw the opposed levers from the disk space leaving only the trial and allowing the trial to be easily decoupled from the insertion instrument.

The installation tool of the present invention can also be provided as a kit having modular components which allow the surgeon to select from among a variety of components to assemble an installation tool that is optimized for its intended use. The kit may include several different levers, drive rods, implant holders, and other elements, each adapted to be used with a particular type or size of implant. For example, the kit can include different types of implant holders, each adapted to mate with a particular prosthesis. A person skilled in the art will appreciate that the installation tool can include a variety of components having a combination of different features. Moreover, the components can be adapted for use with particular types of prosthesis, or for use with other components.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical device installation tool, comprising:
a body having an opening extending therethrough and having grooves formed on opposed sides thereof;
a drive rod adapted to extend through the opening, the drive rod having a proximal end and a distal end with threads formed on at least a portion of a surface thereof;
a pair of opposed levers, each lever extending through one of the grooves in the body and having a proximal end and a distal end, the proximal end of each lever being pivotally coupled to a portion of the body; and
a female threaded member extending across the opening in the body, the female threaded member having a bore formed therein with at least a partial female thread formed in at least a portion of the bore, and the female threaded member being selectively movable between (1) a drive rod rotation configuration in which the partial female thread is engaged with the threads on the rod to permit longitudinal translation of the rod only upon rotation of the rod and (2) a translation configuration to permit longitudinal translation of the rod upon translation of the rod without rotation of the rod, wherein the female threaded member is biased to the drive rod rotation configuration such that releasing the female threaded member from the translation configuration automatically moves the female threaded member to the drive rod rotation configuration.

2. The medical device installation tool of claim 1, wherein the distal end of the drive rod is adapted to engage an implant.

3. The medical device installation tool of claim 1, further comprising an implant holder disposed at the distal end of the drive rod.

4. The medical device installation tool of claim 3, wherein the implant holder has a selectively adjustable height.

5. The medical device installation tool of claim 1, further comprising a handle disposed at the proximal end of the drive rod.

6. The medical device installation tool of claim 1, further comprising a supply of lever pairs of varying sizes and configurations.

7. The medical device installation tool of claim 1, wherein the body includes a handle component at a proximal end thereof.

8. The medical device installation tool of claim 7, wherein the levers are removably coupled to a distal most portion of the body.

9. The medical device installation tool of claim 8, wherein each lever is coupled to a coupling flange formed on a distal facing surface of the body.

10. The medical device installation tool of claim 1, wherein a handle component is disposed at a distal end of the body.

11. The medical device installation tool of claim 10, wherein opposed sides of the handle component have the grooves formed thereon with a coupling flange disposed at a proximal portion of each groove and a stabilizing flange disposed at a distal portion of each groove.

12. The medical device installation tool of claim 11, wherein each lever has a slot formed in at least a portion of a medial side thereof, the slot adapted to seat the stabilizing flange.

13. The medical device installation tool of claim 11, wherein the levers are removably attached within the grooves of the handle component such that a portion of each lever seats both the coupling flange and the stabilizing flange.

14. The medical device installation tool of claim 1, wherein the female threaded member comprises a split nut having two separate sections, each section including a substantially hemispherical groove extending axially therethrough, each hemispherical groove having threads formed on at least a portion thereof.

15. The medical device installation tool of claim 14, wherein the separate sections are biased to a joined position such that the hemispherical grooves are aligned to form the bore and the threads in the hemispherical grooves are adapted to mate with the threads on the drive rod, the bore being substantially cylindrical.

16. The medical device installation tool of claim 15, further comprising a release mechanism adapted to separate the separate sections such that the threads in the hemispherical grooves are unable to mate with the threads on the drive rod.

17. The medical device installation tool of claim 1, wherein the female threaded member comprises a half nut having the bore extending axially therethrough.

18. The medical device installation tool of claim 17, further comprising an engagement member associated with the half nut, the engagement member adapted to maintain the threads of the bore in mating contact with the threads of the drive rod.

19. The medical device installation tool of claim 18, further comprising a release mechanism adapted to separate the threads in the bore from the threads on the drive rod.

20. The medical device installation tool of claim 18, further comprising a locking mechanism associated with the half nut, the locking mechanism adapted to maintain the thread engagement.

21. The medical device installation tool of claim 1, further comprising a release mechanism adapted to move radially inward toward the drive rod to move the female threaded member radially outward away from the drive rod and into the translation configuration.

22. A medical device installation tool, comprising:
a body having a bore extending therethrough and having at least one coupling flange;
a drive rod adapted to extend through the bore, the drive rod having a proximal end and a distal end with threads formed on at least a portion of a surface thereof; and
a pair of opposed levers attached to the at least one coupling flange, each lever having a proximal end and a distal end, the proximal end of each lever being pivotally coupled to a portion of the body; and
the body having at least a partial female thread formed in at least a portion of the bore, the female thread being selectively engageable in (1) a drive rod rotation configuration in which the female thread is engaged with the threads on the rod to permit longitudinal translation of the rod only upon rotation of the rod and (2) a translation configuration to permit longitudinal translation of the rod upon translation of the rod without rotation of the rod wherein the female thread is biased to the drive rod rotation configuration such that releasing the female thread from the translation configuration automatically moves the female thread to the drive rod rotation configuration.

23. The medical device installation tool of claim 22, further comprising a release mechanism adapted to move radially inward toward the drive rod to move the female thread radially outward away from the drive rod and into the translation configuration.

* * * * *